(12) United States Patent
Stratis et al.

(10) Patent No.: US 7,333,897 B2
(45) Date of Patent: Feb. 19, 2008

(54) METHOD AND SYSTEM FOR IDENTIFYING MATERIAL COMPOSITION BASED UPON POLARIZATION TRAJECTORIES

(75) Inventors: Glafkos Stratis, Lake Worth, FL (US); Eric T. Eaton, Lake Worth, FL (US); Salvador Sibecas, Lake Worth, FL (US)

(73) Assignee: Motorola, Inc., Schaumburg, IL (US)

( * ) Notice: Subject to any disclaimer, the term of this patent is extended or adjusted under 35 U.S.C. 154(b) by 25 days.

(21) Appl. No.: 11/296,083

(22) Filed: Dec. 7, 2005

(65) Prior Publication Data

US 2007/0143036 A1  Jun. 21, 2007

(51) Int. Cl.
*G01N 31/00* (2006.01)
(52) U.S. Cl. ......................................... 702/28
(58) Field of Classification Search ................... 702/28
See application file for complete search history.

(56) References Cited

U.S. PATENT DOCUMENTS

| | | | |
|---|---|---|---|
| 3,700,334 A | 10/1972 | Low et al. | |
| 4,659,982 A | 4/1987 | Van de Velde et al. | |
| 6,335,625 B1 * | 1/2002 | Bryant et al. | 324/637 |
| 6,344,818 B1 | 2/2002 | Markov | |
| 6,563,582 B1 | 5/2003 | Chun | |
| 6,972,692 B2 | 12/2005 | Eaton et al. | |
| 6,987,393 B2 * | 1/2006 | Jean et al. | 324/644 |
| 7,047,809 B2 * | 5/2006 | Cobb | 73/599 |
| 2004/0214621 A1 | 10/2004 | Ponce de Leon et al. | |
| 2006/0255277 A1 * | 11/2006 | Cole et al. | 250/341.1 |
| 2007/0046289 A1 * | 3/2007 | Troxler | 324/334 |

OTHER PUBLICATIONS

Agrawal & Boerner, "Redevelopment of Kennaugh's Target Characteristic Polarization State Theory Using the Polarization Transformation Ratio Formalism For the Coherent Case," IEEE, Transactions On Geoscience and Remote Sensing, vol. 27, No. 1, pp. 2-14 (Jan. 1989).

Jian Yang & Yoshio Yamaguchi, et al. "The Characteristic Polarization States and the Equi-Power Curves," IEEE Transactions On Geoscience and Remote Sensing, vol. 40, No. 2, pp. 305-313 (Feb. 2002).

(Continued)

*Primary Examiner*—John Barlow
*Assistant Examiner*—Aditya S. Bhat

(57) ABSTRACT

A system and method for determining a most likely material composition of an object. At least one respective stored radiation polarization transformation is stored for at least one material composition at a plurality of wavelengths. A transmitted electromagnetic signal with at least one wavelength within the plurality of wavelengths and that has a predetermined transmitted polarization profile is transmitted. The transmitted signal encounters an object and is received as at least one received signal. Processing determines a respective received polarization for each of the at least one wavelength of the received signal, determines a respective calculated polarization transformation between the transmitted polarization profile and the received polarization of the respective wavelength, for each of the at least one wavelength. The processing also compares the respective calculated polarization transformations to the at least one respective stored radiation polarization transformations for at least one of the plurality of material compositions and based on those comparisons, estimates a most likely material composition for the object.

20 Claims, 12 Drawing Sheets

OTHER PUBLICATIONS

Xuesong Wang & Shunping Xiao, et al., "Target Recognition Based On Polarization Frequency Stability," Electronic Eng. College of Nat'l Univ. of Def Tech, Changsha, Hunan, P.R. China, pp. 217-220 (IEEE 1996).

Stratis G.K, Naik, V; Boerner W.M; Cole J.B, "WideBand Polarimetric Radar Imaging", Antennas and Propagation Symposium, 1992 AP-S, IEEE, 1992, p. 1130, vol. 2.

Ronald Dilsavor, M.S., BSSEE, Ph.D Thesis, Ohio State University, 1993, "Detection of target scattering centers in terrain clutter using an Ultra-wideband, Fully polarimetric synthetic aperture radar"., abstract only.

D.L. McMakin et al., "Remote Concealed Weapons and Explosive Detection on People Using Millimeter-wave Holography" 1996 IEEE, pp. 19-25.

Stratis et al, "Composite Antenna Pattern For Realistic Ray Tracing Simulations", Antennas and Propagation symposium, IEEE, 2002, Columbus, Ohio., pp. 106-109.

Shilo, et al., W-Band Multibeam Scanning Radiometric System For Contraband Detection Applications, (MSMW'04 Symposium Proceedings, Jun. 21-26, 2004), pp. 881-883.

Roy S. Kalawsky, Polarimetric Image Processing: An Important New Tool For Forensic Science, IEE Colloquium—Electronic Image and Image Processing and Forensic Science (May 22, 1990), pp. 5/1-5/9.

George A. Deschamps & P. Edward Mast, "Poincare Sphere, Representative of Partially Polarized Fields", IEEE Transactions on Antennas and Propagation, vol. AP-21, No. 4 (1973), pp. 474-478.

Howard A. Zebker & Jakob J. Van Zyl, "Imaging Radar Polarimetry: A Review", Proceedings of the IEEE, vol. 79, No. 11 (Nov. 1991), pp. 1583-1606.

Yoshio Yamaguchi, Masakazu Sengoku, Takeo Abe, "*FM-CW Radar Applied To The Detection Of Buried Objects In Snowpack*," Dept. of Info. Eng., Niigata Univ.Niigata, 950-21 Japan, pp. 738-741. (IEEE 1990).

* cited by examiner

|  | $F_a$ | $F_B$ | $F_C$ | $F_D$ | $F_E$ | $F_F$ |
|---|---|---|---|---|---|---|
| MAT$_1$ | $M_{1a}$ | $M_{1B}$ | $M_{1C}$ | $M_{1D}$ | $M_{1E}$ | $M_{1F}$ |
| MAT$_2$ | $M_{2a}$ | $M_{2B}$ | $M_{2C}$ | $M_{2D}$ | $M_{2E}$ | $M_{2F}$ |
| MAT$_3$ | $M_{3a}$ | $M_{3B}$ | $M_{3C}$ | $M_{3D}$ | $M_{3E}$ | $M_{3F}$ |

METHOD AND SYSTEM FOR IDENTIFYING MATERIAL COMPOSITION BASED UPON POLARIZATION TRAJECTORIES

FIELD OF THE INVENTION

The present invention relates generally to the field of material identification techniques and systems, and more particularly relates to identifying a type of material based upon its electromagnetic re-radiation properties.

BACKGROUND OF THE INVENTION

Rapid and accurate identification of materials is a requirement of many applications, particularly for identification of dangerous devices such as explosives. Security checkpoints, such as found in airports and entrances to other sensitive areas, benefit from being able to determine if an object contains or is made of explosive or otherwise dangerous material. Techniques used to identify objects include X-Ray equipment, holographic image processing devices, and ionizing radiation detectors to identify radioactive materials. X-ray and holographic methods have a drawback of being limited to identifying the shape of an item, but give no information regarding the composition of the material that makes up the item. Ionizing radiation detectors identify radioactive material, but do not detect conventional explosive devices. X-ray and holographic systems are often large, immobile devices that require fixed installations, thereby limiting the flexibility of their use.

Therefore a need exists to overcome the problems with the prior art as discussed above.

SUMMARY OF THE INVENTION

Briefly, in accordance with the present invention, disclosed is a method for determining a most likely material composition of an object that includes storing at least one respective stored radiation polarization transformation for each material compositions within the at least one material composition. The method further includes transmitting a transmitted electromagnetic signal with at least one wavelength that is within the plurality of wavelengths. The transmitted electromagnetic signal having a predetermined transmitted polarization profile. The method also includes receiving at least one received signal at the at least one wavelength after the transmitted signal has encountered an object. The method further includes determining a respective received polarization for each of the at least one wavelength of the received signal and determining, for each of the at least one wavelength, a respective calculated polarization transformation between the transmitted polarization profile and the respective received polarization of the respective wavelength. The method also includes comparing, for each of the at least one wavelength, the respective calculated polarization transformations to the at least one respective stored radiation polarization transformations for at least one of the plurality of material compositions and estimating, based on the comparing, a most likely material composition for the object.

Also disclosed is a material determination system used to determine a most likely material composition of an object that includes a stored transformation database that stores, for at least one material composition, at least one respective stored radiation polarization transformation at a plurality of wavelengths for each of the material compositions within the at least one material composition. The material determination system also includes a transmitter that transmits a transmitted electromagnetic signal with at least one wavelength within the plurality of wavelengths. The transmitted electromagnetic signal having a predetermined transmitted polarization profile. The material determination system also includes a receiver that receives at least one received signal at the at least one wavelength, after the signal has encountered an object. The material determination system further includes a material composition estimator that a) determines a respective received polarization for each of the at least one wavelength of the received signal, b) determines, for each of the at least one wavelength, a respective calculated polarization transformation between the transmitted polarization profile and the respective received polarization of the respective wavelength, c) compares, for each of the at least one wavelength, the respective calculated polarization transformations to the at least one respective stored radiation polarization transformations for at least one of the plurality of material compositions, and d) estimates, based on the comparing, a most likely material composition for the object.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 5 illustrates a measured polarization transformation to material mapping table, in accordance with one embodiment of the present invention.

DETAILED DESCRIPTION

Figure 1:
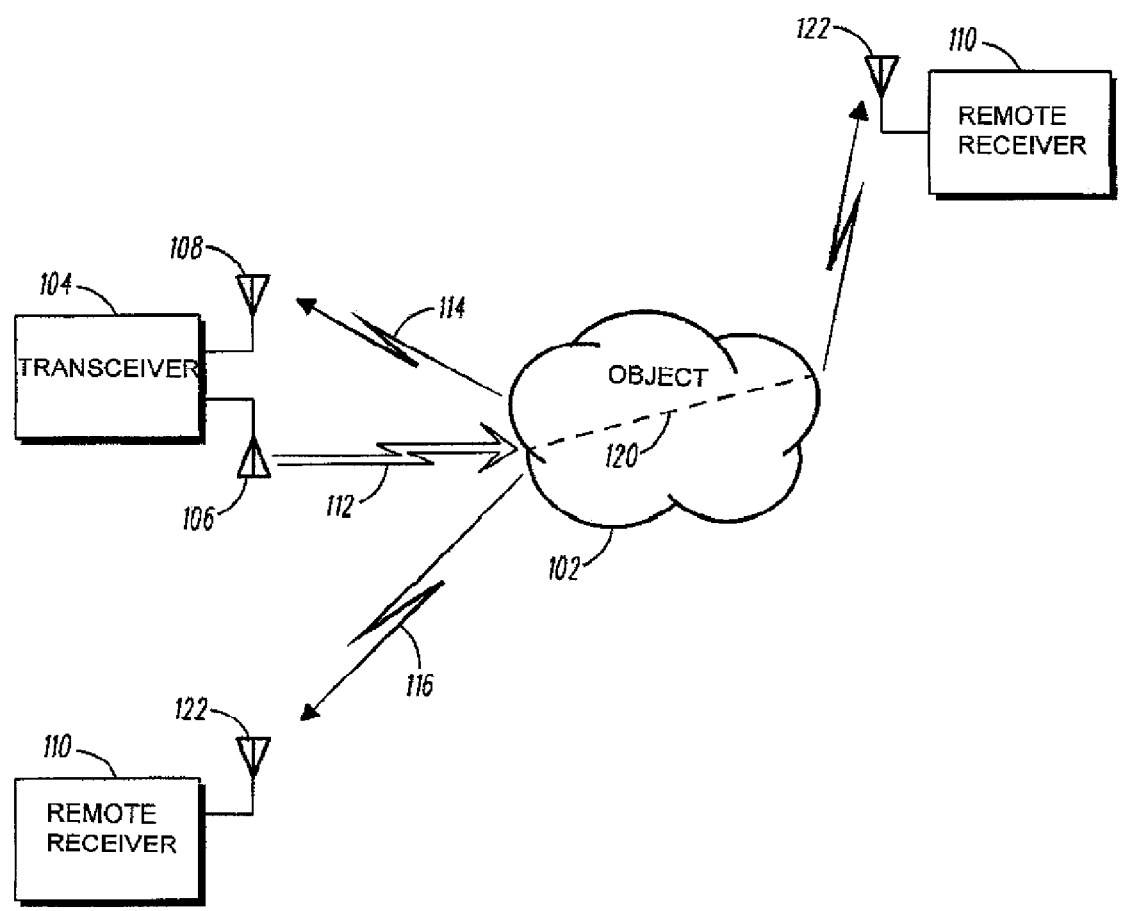
FIG. 1 illustrates an operational environment for a material determination system in accordance with one embodiment of the present invention.

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

While the specification concludes with claims defining the features of the invention that are regarded as novel, it is believed that the invention will be better understood from a consideration of the following description in conjunction with the drawing figures, in which like reference numerals are carried forward.

FIG. 1 illustrates an operational environment for a material determination system 100 in accordance with one embodiment of the present invention. The material determination system 100 of the exemplary embodiment includes a signal transceiver 104 that transmits modulated or unmodulated transmitted electromagnetic signals 112 that have a pre-determined electro-magnetic polarization profiles. The exemplary material determination system 100 uses radio frequency signals to estimate a material composition of an object. Further embodiments of the present invention are able to use any electromagnetic signals with predetermined polarization characteristics, such as light, X-ray, extremely short wavelength electromagnetic radiation, and ultra-low frequency electromagnetic radiation signals.

The transmitted electromagnetic signals 112 of the exemplary embodiment are broadcast by a transmitter antenna 106. The transmitter antenna 106 of the exemplary embodiment supports complete control and adjustment of the polarization of the transmitted electromagnetic signals 112, as is described in more detail below. Further embodiments of the exemplary embodiment are able to operate with fixed transmitted polarizations or with limited adjustment of the transmitted polarizations. These transmitted electromagnetic signals 112 are directed towards a physical object 102 in order to determine the material composition of that physical object 102. As an example, the operation of the material determination system is able to identify if the physical object 102 is made of steel, one of various types of plastic, an explosive material, or other types of material. The transmitted electromagnetic signals 112 are transformed as they encounter, i.e., pass near, are refracted, diffracted or reflected by, the physical object 102. This transformation is caused by being either reflected from, refracted by or diffracted by the physical object 102. In being refracted, the transmitted electromagnetic signals 112 impinges upon the physical object 102 and surface currents 120 are sometimes able to develop that transform the electromagnetic signal prior to being a refracted/diffracted electromagnetic signal 118. The exemplary embodiment of the present invention operates by observing electromagnetic waves that are reflected from an object. One manifestation of the transformation of the electromagnetic signals as they are reflected, refracted or diffracted by the physical object 102 is a change in the electromagnetic wave polarization. These changes in polarization are measured and analyzed by the processing of the exemplary embodiment. The operation of the material determination system 100 is able to place the physical object 102 in either the near field or far field of the transmitter antenna 106.

The receiving elements of the material determination system 100 include the signal transceiver 104, which includes a receiving antenna 108, and remote receivers 110, which have associated remote receiving antennas 122. The signal transceiver 104 receives a monostatic reflected received signal 114 that is reflected from the object 102. The remote receivers 110 of the exemplary embodiment are able to be located relative to the signal transceiver 104 and the physical object 102 so as to receive either reflected electromagnetic signals 116 or refracted/diffracted electromagnetic signals 118 and create a bi-static signal receiving and processing system. The remote receiving antennas 122 of the remote receivers 110 and the receiving antenna 108 of the transceiver 104 in the exemplary embodiment include a pair of antennas with orthogonal electromagnetic polarization so as to be able to support processing to analyze and determine the electromagnetic polarization of received electromagnetic signals, such as reflected received signal 116 or reflected/refracted received signal 118. Further embodiments of the present in invention incorporate antennas that are not orthogonal to one another but that do include orthogonal components, such as two linearly polarized antennas that are offset by 45 degrees. The processing of the exemplary embodiment compares the determined received electromagnetic signal polarization with the polarization of the transmitted signal 112 to determine the polarization transformation caused by the physical object 102. The determined polarization transformation is compared to stored values that were previously obtained by measuring polarization transformations caused in various transmitted signals by various materials.

The processing of the exemplary embodiment of the present invention detects the type of material a physical object 102 is made of though the use of observed electromagnetic signal polarization trajectories characteristics for various material types. In the context of the present disclosure, a polarization trajectory refers to a change in electromagnetic signal polarization that is caused by encountering an object. Embodiments of the present invention use and measure polarization trajectories for either a single wavelength transmitted electromagnetic signal or for a multi-wavelength spectrum that is able to have either a continuous frequency spectrum, such as achieved by wideband modulation of a single RF carrier, or a non-continuous frequency spectrum, such as is generated by transmitting a number of unmodulated or narrow band modulated RF carriers. As an example, a vertically polarized antenna (in free space) is used to transmit transmitted electromagnetic signal 112, which will thereby have a vertical polarization. The reflected electromagnetic signal 116 has different polarizations at various wavelengths due to the polarization transformation caused by the physical object 102. The polarization transformation caused by the physical object is dependent upon the wavelength of the transmitted electromagnetic signal 112 being reflected. As a simple example, a linearly vertically polarized signal may be reflected from an object as a linearly horizontally polarized signal at a particular wavelength. Such a case produces a polarization trajectory of ninety degrees.

The polarization of electromagnetic waves is well known in the relevant arts. The definitions used in this specification are based upon IEEE standard (145-1983), which defines antenna orientation with respect to the orientation of the electric field components, and the associated coordinate system. Polarization of an electromagnetic wave describes the motion (i.e., oscillation) and orientation of the electric field vector components in space-time according to the co-ordinate system. A plane wave traveling through a depolarizing medium will emerge with a potentially altered polarization. An example using the three orthogonal axes X-Y-Z has a vertically polarized wave oriented along the X axis with a direction of propagation along the Z direction. This is an example of a vertically polarized wave since the electric field vector is perpendicular on the Y-Z plane. As the wave encounters, i.e., passed through or near, a depolarizing medium, the total electric field vector rotates and causes the resulting polarization to be not purely vertical. The degree of depolarization depends on the wavelength of the incident signal, the type of material and shape of the depolarizing medium.

Figure 2:
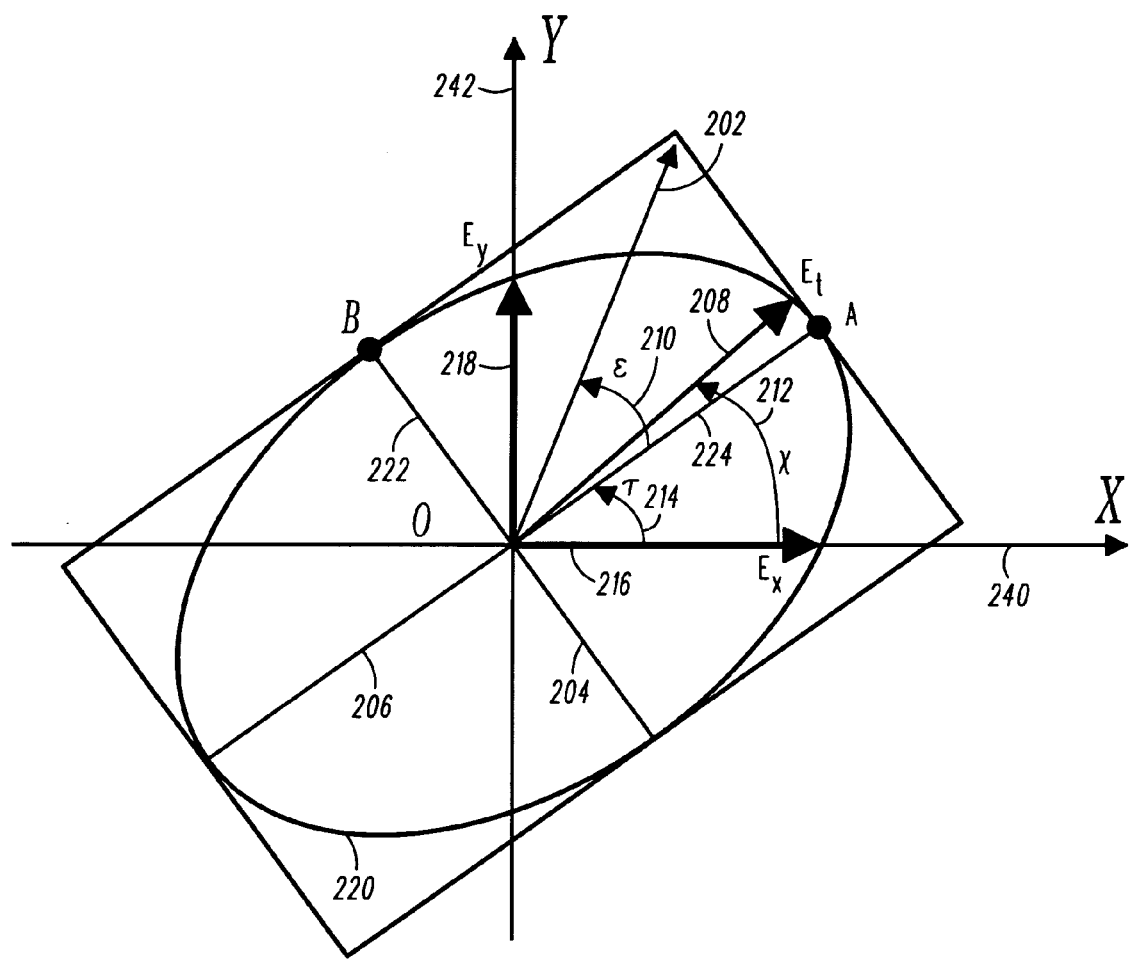
FIG. 2 illustrates an elliptical polarization dimensional analysis as used by processing of an exemplary embodiment of the present invention.

FIG. 2 illustrates an elliptical polarization dimensional analysis 200 as used by processing of an exemplary embodiment of the present invention. The illustrated polarization dimensional analysis shows the relationship of a signal's electric field components relative to the reference coordinate system represented by the X axis 240 and the Y axis 242. The total electric field $E_t$ 208 is a vector sum of the vertical electric field $E_x$ 218 and the horizontal electric field $E_y$ 216. This relationship is given by the following equation:

$$\vec{E}_t = E_x \vec{x} + E_y \vec{y}$$

Where:

$$E_x = E_1 \cos(\omega t)$$

$E_y = E_2 \cos(\omega t)$, where $E_1$ and $E_2$ are the amplitudes of the instantaneous electric fields.

As the electric field of $E_t$ 208 oscillates, the polarization of the associated electromagnetic signal traces an ellipse 220 with a major axis OA 224 and Minor Axis OB 222. The ratio "R" of these axes is described by the following equation.

$$R = \frac{E_{major}}{E_{minor}} = \frac{OA(224)}{OB(222)} \geq 1$$

A value of "R" that is grater than zero indicates right-hand circular or elliptical polarization and a value of "R" that is less than zero indicates left hand circular or elliptical polarization. The ellipticity angle $\epsilon$ 210 for this exemplary electromagnetic signal is given by the following equation.

$$\epsilon = \cot^{-1}(-R), \quad -45° \leq \epsilon \leq 45°$$

The "tilt angle" $\tau$ 214 of this exemplary electromagnetic signal is given by the following equation:

$$\tau = \tan^{-1}\left(\frac{E_y}{Ex}\right), \quad 0° \leq \tau \leq 180°$$

Figure 3:
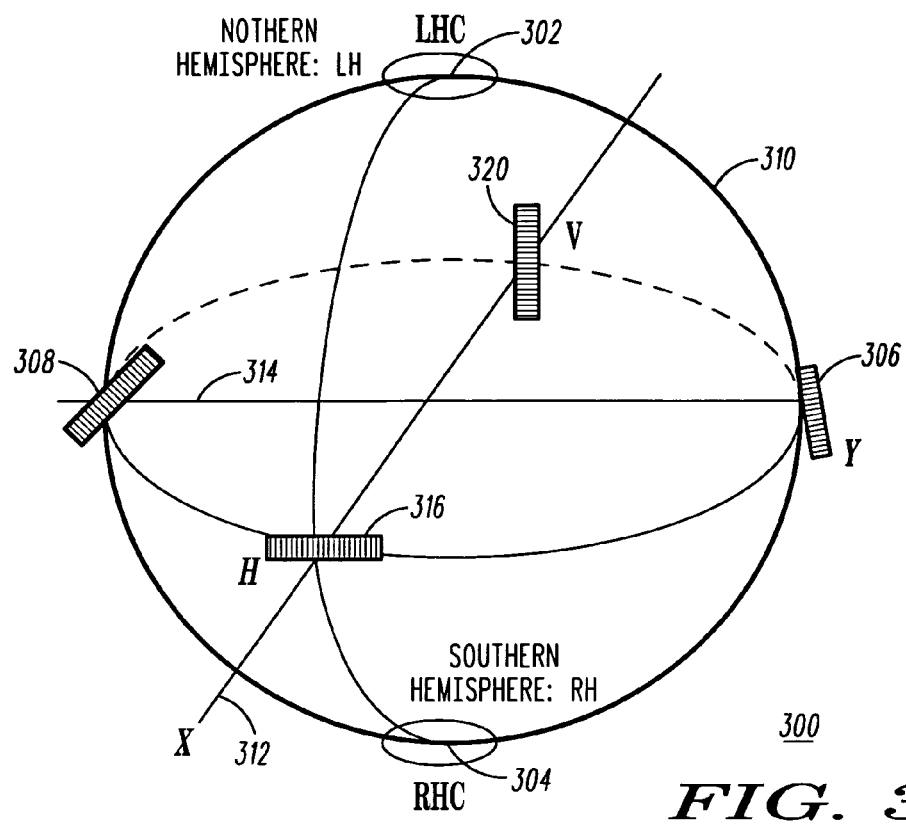
FIG. 3 is a Poincare' sphere illustration of polarization values as used by processing of an exemplary embodiment of the present invention.

FIG. 3 is a Poincare' sphere illustration 300 of polarization values as used by processing of an exemplary embodiment of the present invention. As is known in the art, the Poincare' sphere 310 represents the polarization state of an electromagnetic signal. Any polarization state can be generated from a combination a horizontal linearly polarized electromagnetic signal and a vertical linearly polarized signal by varying the relative amplitude and phase of those two linearly polarized signals.

The Poincare' sphere illustration 300 shows several exemplary polarization states. A purely horizontal linearly polarized signal location 316 and a purely vertical linearly polarized signal location 320 are shown to lie on the equator of the Poincare' sphere. The purely horizontal linearly polarized signal location 316 and purely vertical linearly polarized signal location 320 lie along the "X" axis 312 shown in this example. Also on the equator is are a forty-five degree left tilt polarization location 306 and a forty-five degree left tilt polarization location 308. The forty-five degree left tilt polarization location 306 and forty-five degree left tilt polarization location 308 lie along the "Y" axis 314 shown in this example. A Left Hand Circular (LHC) location 302 and a Right Hand Circular (RHC) location 304 are also shown. Points in the upper half of the Poincare' sphere, i.e., the "northern hemisphere," are left hand circular or elliptically polarized and points in the lower half of the Poincare' sphere, i.e., the "southern hemisphere," are right hand circular or elliptically polarized.

Figure 4:
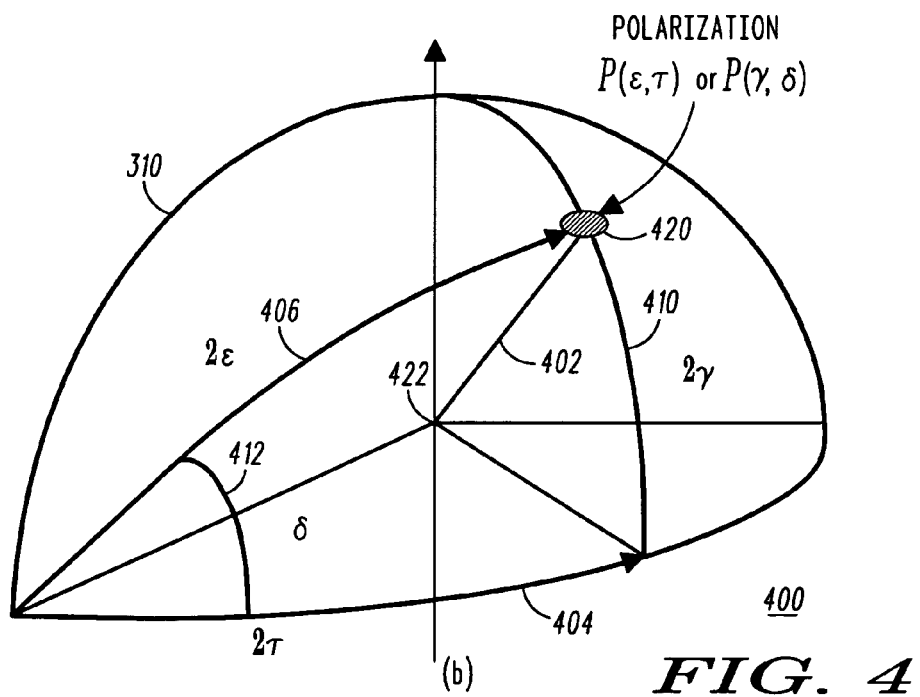
FIG. 4 illustrates spherical dimensions used in analysis performed by processing of an exemplary embodiment of the present invention.

FIG. 4 illustrates spherical dimensions 400 used in analysis performed by processing of an exemplary embodiment of the present invention. The relationships and values of the illustrated spherical dimensions 400 are angles for a vector 402 that extends from the center 422 of the Poincare' sphere 310 to a point 420 that describes the polarization of a particular electromagnetic signal. The illustrated angles include $2\gamma$ 410, $2\tau$ 404, $2\epsilon$ 406, and $\delta$ 412. These angles are determined by the following equations.

$$\gamma = \tan^{-1}\left(\frac{E_y}{Ex}\right), \quad 0° \leq \gamma \leq 90°$$

$$2\tau = \tan^{-1}\left[\frac{\sin(2\gamma)\cos(\delta)}{\cos(2\gamma)}\right]$$

$$2\varepsilon = \sin^{-1}[\sin(2\gamma)\sin(\delta)]$$

Stokes parameters representation is useful for mapping partial polarizations. The use of Stokes parameters is also advantageous since they do not require complex number representations, especially when used on a Poincare sphere. Stokes parameters can be written in terms of spherical co-ordinates and therefore map the polarization states on a sphere, allowing the analysis of trajectories on the Poincare sphere and therefore the dynamic behavior of polarization in relationship to the scattering or depolarization environment used by the exemplary embodiments of the present invention. Stoke's parameters (i.e., polarization states) can be written in the following form.

$$[S] = \begin{bmatrix} 1 \\ S_1 \\ S_2 \\ S_3 \end{bmatrix}$$

Where $s_1 = \cos(2\varepsilon)\cos(2\tau)$ $s_2 = \cos(2\varepsilon)\sin(2\tau)$ $s_3 = \sin(2\varepsilon)$ The exemplary embodiment represents the stored radiation polarization transformations and each of the calculated polarization transformations as the above defined Stoke's parameters. The exemplary embodiment also computes the polarization trajectories, transformations and displacements described below through the use of Stoke's parameters. The comparison of received polarizations to stored values is also facilitated in the exemplary embodiment by their representation through Stoke's parameters.

Another important parameter used especially in polarization measurements is the so called polarization ratio ζ and its relation to the phase difference. The polarization ratio ζ is given by the following equation, where δ is the phase difference between the vertical and horizontal linearly polarized components of the electromagnetic signal.

$$\varsigma = \frac{E_y}{E_x} e^{j\delta}$$

In the general case, a plane wave that is incident on a surface is able to experience changes in 1) the ratio between the amplitudes of the vertical and horizontal components, 2) the phase of these two components, or 3) both the magnitude and phase ratios between these two components may change. As an example, a wave that is incident on a pure metallic surface generally only experiences changes in the relative phase of horizontal and vertical components. In general, the shift in the location of the polarization state on the Poincare sphere of an electromagnetic signal at a particular wavelength from before the signal encounters an object until after the signal is influenced by the object reveals the nature of the material. Since the polarization transformation due to the transmission or reflection of the electromagnetic signal by the object is wavelength dependent, the ratios of the vertical and horizontal components of the reflected electromagnetic signal are also different for different wavelengths as the polarization of the signal is affected by the object. The same material composition of an object therefore produces different shifts in location on the Poincare' sphere for different wavelengths. The exemplary embodiments of the present invention take advantage of this characteristic to identify the material from which the object is made.

The exemplary embodiment of the present invention that is described below transmits a transmitted electromagnetic signal 112 that includes radio signals with at least three center frequencies, or wavelengths, that are able to be modulated to provide a finite spectral bandwidth. Each of these center frequencies are referred to as signal components. Further embodiments are able to use a single radio frequency or wavelength while yet further embodiments are able to use any number of wavelengths, including two, four and so on. As discussed above, a particular material will transform the polarization for a particular wavelength from it's initial, transmitted polarization, i.e., one point on the Poincare' sphere, to another polarization that is represented by another point on the Poincare' sphere. This shift in polarization is represented by a vector from the initial polarization, as represented on the Poincare' sphere, to the transformed polarization after encountering the object, as is represented on the Poincare' sphere.

In order to simplify notation and explanation of the exemplary embodiment, a transmitted electromagnetic signal 112 will be discussed that has vertical polarization. It is clear that any transmitted electromagnetic signal polarization can be utilized in embodiments of the present invention. In general terms, the transmitted electromagnetic signal 112 is able to have polarizations that vary according to wavelength and time varying. The particular transmitted electromagnetic polarization of the transmitted electromagnetic signal 112, which is generally varying by wavelength and time, is referred to as a predetermined transmitted polarization profile for the transmitted electromagnetic signal 112.

When a physical object 102 is illuminated with a transmitted electromagnetic signal 112 that has three frequencies or wavelengths, represented as F1, F2 and F3, the polarization transformation for each of those three wavelengths will generally be different due to the wavelength selective polarization transformation characteristics of the material from which the physical object 102 is made. In the following discussion, the polarization of each electromagnetic wavelength contained in the received signal, including reflected received signal 116, and refracted/diffracted electromagnetic signal 118, is referred to as a respective received polarization that is associated with the particular wavelength.

The following notation is used to represent the polarization transformation for the three exemplary wavelengths from their initially transmitted polarization to their transformed, or shifted, polarization of the received signal, including the reflected electromagnetic signal 116 or the refracted/diffracted electromagnetic signal 118. These polarization transformations are depicted as translations of points along the surface of the Poincare' sphere. In this exemplary case, the initially transmitted polarization for all of the three wavelengths is the same. This is not a requirement for the operation of embodiments of the present invention. In the more general case, the polarization transformation that is used by the exemplary embodiment is the change in polarization from the polarization of a particular wavelength contained within the transmitted signal 112, at a particular wavelength, to the respective received polarization of the respective wavelength within the received signal. These differences between the polarization of a respective wavelength of the transmitted electromagnetic signal 112, as defined by the predetermined transmitted polarization profile, and the respective received polarization, as are calculated for each wavelength of interest in the transmitted electromagnetic signal in the exemplary embodiment, are referred to herein as respective calculated polarization transformations.

In the simplified example used for ease of understanding in this specification, the initial polarization of all wavelengths transmitted within the transmitted electromagnetic signal 112 is indicated as Fsp to indicate the polarization in "free space" (sp). The transformed polarization for the three wavelengths contained in the received signal, which have been transformed by encountering the physical object 102, are indicated as: "f1," "f2," and "f3," respectively. This results in the polarization of the electromagnetic signal in this example being transformed from the initial polarization, Fsp, to "f1," "f2," and "f3." This transformation reflects a shift of the polarization depicted on the Poincare' sphere from Fsp to f1, f2 or f3. These translations can be specified by a respective vector from the point Fsp on the Poincare' sphere to the each of the points f1, f2, and f3 for the respective radio frequency and corresponding wavelength. The following discussion represents these vectors as:

Trajectory from Fsp to f1=f11
Trajectory from Fsp to f2=f22
Trajectory from Fsp to f3=f33

The above example is based upon the simple case of this description where the electromagnetic signals for the three wavelengths are all transmitted at the same polarization. This is not a requirement and therefore the more general case uses f11, f22 and f33 to represent the vector for the polarization translation from transmission to reception of the respective wavelength along the surface of the Poincare' sphere.

In addition to the translation from the initially transmitted polarization to the transformed polarization for each transmitted wavelength of interest, the processing of the exemplary embodiment further calculates vectors that correspond to the displacement between each of the three polarizations f11, f22 and f33 themselves. In the simplified example discussed above, the vector f12 reflects the translation from f11 to f22, the vector f13 reflects the translation from f11 to f33, and the vector f23 reflects the translation from f22 to f33. It is clear that the translation between these two points in the other direction is also indicated by, for example, f21, f31, and f32, respectively. In the generalized case where the different wavelengths are able to have different initial, or transmitted, polarizations, these vectors are simply the victor difference between the f11, f22 and f33 vectors that are described above.

Polarization displacements used by the exemplary embodiment included stored polarization displacement data that is pre-determined for at least material type that is a candidate for estimation. The exemplary embodiment further calculates determined polarization displacements from the received signals to characterize the physical object 102. The processing compares the determined polarization displacements to the stored polarization displacement data to support identification of the material of which the physical object 102 is constructed. Some embodiments of the present invention base this estimation only upon the polarization displacement data.

The processing of the exemplary embodiment represents polarization translation vectors as a Polarization Trajectory State Space Matrix, "m," which is constructed as follows.

$$m = \begin{matrix} f11 & f12 & f13 \\ f21 & f22 & f23 \\ f31 & f32 & f33 \end{matrix}$$

The size of the Polarization Trajectory State Space Matrix, "m" is determined by the number of radio frequency signals, or wavelengths of interest, used by the particular embodiment or for a particular representation. The above example uses three radio frequencies, or wavelengths, and therefore has a 3×3 Polarization Trajectory State Space Matrix, "m." The use of "n" wavelengths will result in the use of an n×n matrix. The Polarization Trajectory State Space Matrix, "m," represents a split of polarization states that is similar to the split of eigen-states in quantum mechanics or solid state theory. The depolarizing state trajectory space among the wavelengths with respect to each other—<f12, f21>, <f13, f31> and <f23, f32>—represent the off diagonal matrix elements and are referred to as trajectories, or displacements, between these points on the Poincare' sphere. The polarization state space is referred to by these vectors as the magnitude and phase changes between vertically polarized and horizontally polarized electromagnetic signals. That state space, in combination with the various trajectories and displacements, gives a unique description of the material type or identity.

It is important to note that the polarization state space required to move, for example, from f2 back to f1, may not be reciprocal in certain cases, e.g., the trajectory may not be the same. In other words, to go back from f2 to f1 the polarization factor could be different compared to the polarization factor from f1 to f2. This is another parallelism with Quantum theory where after the energy splits in discrete eigen states and when it comes back to the original state, it does not necessarily come back from the same path. The same scenarios happen with the rest of the polarization state space locations corresponding to the off diagonal elements i.e. <f13, f31> and etc. Remember that number of wavelengths of interest determines the size of the matrix; for example, using four wavelengths results in the use of a 4×4 matrix.

The exemplary embodiments of the present invention transmit transmitted electromagnetic signals 112 that have one or more RF carrier signals that each has a pre-determined center radio frequency and corresponding wavelength. Each of these RF carrier signals is able to be modulated so as to produce a desired frequency domain characteristic for the transmitted electromagnetic signal. For example, transmission pulses are able to be used to give each carrier an approximately Sinc shaped frequency spectrum for the transmitted radio frequency signals. Shaped pulses or other modulating waveforms can also be used to tailor the transmitted frequency as desired. The transmitted electromagnetic signal 112 is able to be modulated by a predetermined waveform. This predetermined waveform is able to be, for example, a uniform pulse train at one or more specific wavelengths or a pulse train that has one or more of RF wavelength, timing, and/or polarization selected according to a pseudo-noise (PN) data sequence. In the case of the exemplary embodiment, data defined by fields within a PN data sequence are used to index into a table of RF wavelength, polarization and pulse timing to create a pseudo-random sequence of these characteristics. A pseudo-noise generated data sequence can be further used to generate a more arbitrary predetermined waveform, such as a waveform with varying amplitude, phase, multiple sub-carriers, and the like. The transmitted electromagnetic signal 112 is able to consist of one or more RF carriers. Each of these RF carriers is able to be modulated with any desired waveform to produce a desired RF frequency spectrum. Receivers of the exemplary embodiment are able to recreate a synchronized version of the pseudo-random sequence used by the transmitter to allow for proper reception of reflected electromagnetic signals. Synchronization of the pseudo-random sequence at a receiver is able to be accomplished through processing of received signals or through synchronization data that is communicated to the remote receivers over a suitable communications channel.

FIG. 5 illustrates a measured polarization transformation to material mapping table 500, in accordance with one embodiment of the present invention. This exemplary measured polarization transformation to material mapping table 500 includes data for three types of materials, corresponding to row $MAT_1$ 514, row $MAT_2$ 516 and row $MAT_3$ 518. The illustration of only three types of material is for ease of understanding and simplicity of representation in this specification. The exemplary embodiment of the present invention is stored in a stored transformation database within the exemplary embodiment and contains polarization transformation data that has been measured for many types of materials.

The polarization transformation to material mapping table 500 illustrates six sets of radio frequency, or wavelength, sets that are used to estimate the type of material from which an object is constructed. These six frequency sets are represented by the columns for $F_a$ 502, $F_b$ 504, $F_c$ 506, $F_d$ 508, $F_e$ 510, and $F_f$ 512. The frequency sets of each column of the polarization transformation to material mapping table 500 correspond to transmitted electromagnetic signals 112 that include different sets of center radio frequencies, or wavelengths, or that use particular modulation waveforms for the RF carriers. As an exemplary configuration, frequency set $F_a$ is able to include, for example, three RF carriers that each has a specific pulse modulation. Frequency set $F_b$ is able to include, for example, three different RF carrier frequencies that are different than those of $F_a$, where each RF carrier has a specific pulse modulation. Frequency set $F_c$ is able to include, for example, three RF carriers that each has different center frequencies and modulation waveforms than those of $F_a$. Frequency set $F_d$ is able to include, for example, five RF carriers that each has a specific pulse modulation. Frequency set $F_e$ is able to include, for example, five RF carriers with different modulating waveforms that those of $F_d$. Frequency set $F_f$ is able to include, for example, a continuous RF spectrum that covers a wide bandwidth. The use of an RF carrier that is modulated to have a wide RF bandwidth allows the polarization transformation characteristics to be measured across the RF bandwidth of that RF carrier. The wavelengths to be transmitted and which are characterized by the polarization transformation data are able to be selected based upon an amount of polarization transformation exhibited by one or more of the materials for those selected radio frequencies or wavelengths. The use of a wide bandwidth RF carrier allows simultaneous test and measurement of polarization transformation at points across the bandwidth of the RF carrier and thereby to allow potentially optimal testing for many different materials. Some embodiments of the present invention are able to transmit a broadband electromagnetic signal, such as a single carrier modulated by a wide bandwidth signal, and limit processing to only selected portions of the frequency spectrum of the received reflected signal. In such embodiments, the selected separate portions of the received signal that are processed are comparable to at least two of the plurality of wavelengths that are processed as discussed above. The polarization transformation to material mapping table 500 is also able to store polarization transformation data that corresponds to having object 102 in the near field of the transmitter antenna 106 or a receiving antenna, such as receiving antenna 108 or remote receiving antenna 122. The use of such data is able to be facilitated by, for example, prompting an operator to place a device containing one or both of the transmitter antenna 106 and the receiving antenna 108 near the object 102 to be characterized.

The polarization transformation to material mapping table 500 stores a Polarization Trajectory State Space Matrix, "m" for each frequency set—material pair, as indicated by, for example, $m_{1a}$, $m_{1b}$, and so forth. The Polarization Trajectory State Space Matrices of the exemplary embodiment are determined through empirical means for each material and frequency set. Initial determination of the Polarization Trajectory State Space matrices includes testing various material compositions to determine the polarization transformation for the various frequencies and modulations included in the respective frequency set.

Figure 6:
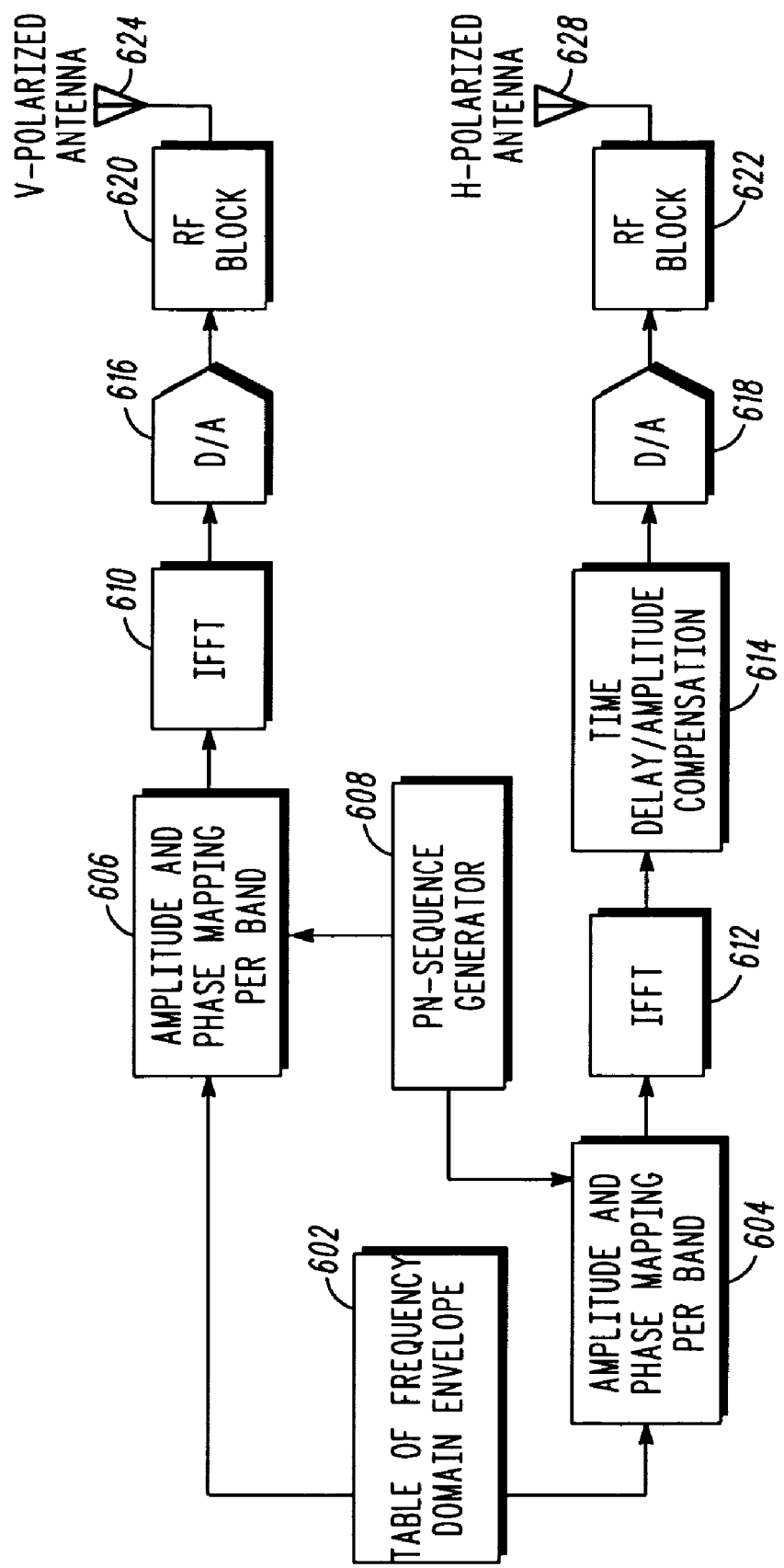
FIG. 6 illustrates a processing block diagram of a frequency domain transmitted signal generation circuit in accordance with one embodiment of the present invention.

FIG. 6 illustrates a processing block diagram of a frequency domain transmitted signal generation circuit 600 in accordance with one embodiment of the present invention. The frequency domain transmitted signal generation circuit 600 generates a transmitted electromagnetic signal 112 and allows specification of the frequency domain envelope for that generated transmitted electromagnetic signal 112. The frequency domain transmitted signal generation circuit 600 includes a vertically polarized antenna 624 and a horizontally polarized antenna 628. The frequency domain transmitted signal generation circuit 600 independently generates two RF signals, one to be transmitted through the vertically polarized antenna 624 and another to be transmitted through the horizontally polarized antenna 628.

The frequency domain transmitted signal generation circuit 600 includes a table of frequency domain envelope 602. The table of frequency domain envelope 602 specifies a discrete frequency domain representation of an RF spectrum for the transmitted electromagnetic signal 112. The table of frequency domain envelope 602 in the exemplary embodiment includes separate entries for the amplitude and phase across the transmitted frequency spectrum for each of the horizontally and vertically polarized transmitted electromagnetic signals. An example of data contained within a table of frequency domain envelope 602 includes RF frequency bands in which constant amplitude, but potentially varying phase, signals are to be generated. Such a transmitted waveform is referred to herein as "frequency pulses" since the frequency domain representation for this signal resembles a time domain pulse train.

The table of frequency domain envelope 602 provides the specification of the complex value, i.e., both magnitude and phase information, of the frequency domain envelope for the vertical and horizontal polarization to a vertical amplitude and phase mapping per band block 606 and a horizontal amplitude and phase mapping per band block 604, respectively. The vertical amplitude and phase mapping per band block 606 and a horizontal amplitude and phase mapping per band block 604 each include a table of multiple entries that define a number of magnitude and phase combinations for their respective transmit polarization signal. Variation of the magnitude and phase of each signal transmitted by the V-polarized antenna 624 and the H-polarized antenna 628 allows adjustment and setting of the transmitted polarization profile for the transmitted electromagnetic signal 112.

The vertical amplitude and phase mapping per band block 606 and a horizontal amplitude and phase mapping per band block 604 also receive a pseudo-noise (PN) data sequence from PN-sequence generator 608. The data contained in the PN data sequence is used by the vertical amplitude and phase mapping per band block 606 and a horizontal amplitude and phase mapping per band block 604 to select one of the magnitude and phase entries stored therein. The selected magnitude and phase entry selected based upon the PN data sequence produces a frequency domain representation of the desired transmitted waveform for each polarization, and thereby varies the predetermined transmitted polarization profile over time.

The output of the vertical amplitude and phase mapping per band block 606 is provided to a vertical Inverse FFT block 610 to produce a digital representation of the time domain signal to be transmitted with vertical polarization. The horizontal amplitude and phase mapping per band block 604 drives a time delay/amplitude compensation module 614 that compensates for time delay and amplitude differences between the vertical and horizontal channels. The vertical Inverse FFT block 610 and the time delay/amplitude compensation module 614 each drive a respective digital to analog (D/A) converter, the vertical D/A 616 and the horizontal D/A 618. The outputs of the D/A converters are provided to a vertical RF block 620 and a horizontal RF block 622, which produces the RF signals for transmission on their respective polarizations through a vertically polarized transmission antenna 624 and a horizontally polarized transmission antenna 628.

Figure 7:
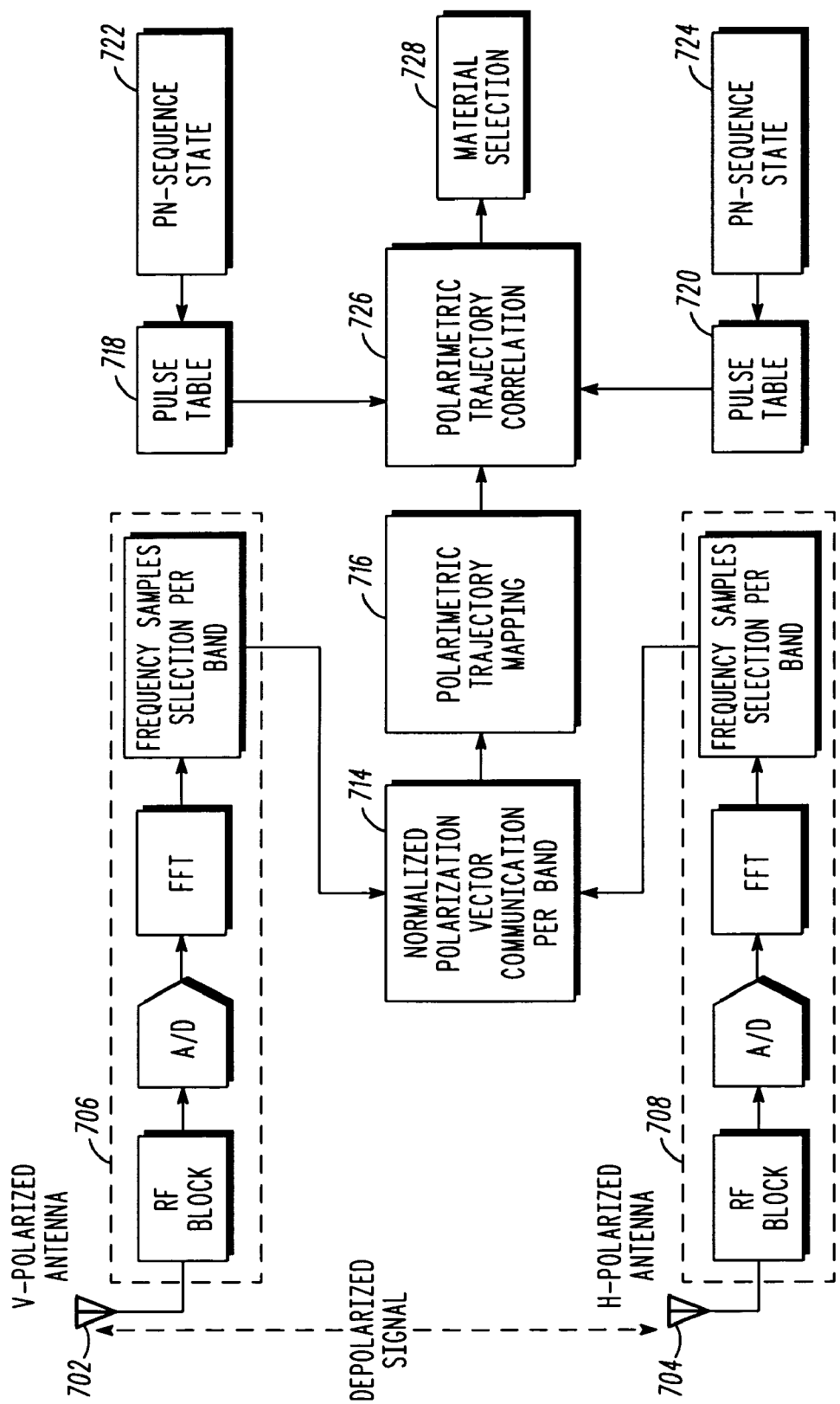
FIG. 7 illustrates a processing block diagram of a frequency domain received signal processing circuit in accordance with one embodiment of the present invention.

FIG. 7 illustrates a processing block diagram of a frequency domain received signal processing circuit 700 in accordance with one embodiment of the present invention. The frequency domain received signal processing circuit 700 receives signals that are reflected, refracted or diffracted by the physical object 102, depending upon the location of its receiving antennas. The frequency domain received signal processing circuit 700 includes receiving antennas that include a vertically polarized receiving antenna 702 and a horizontally polarized receiving antenna 704. The receiving antennas each drive a respective RF signal processing chain, a vertical RF processing chain 706 and a horizontal RF processing chain 708. Each RF processing chain includes an RF block, an Analog to Digital converter (A/D), a Fast Fourier Transform (FFT) processor and a frequency samples selection per band processor. The RF processing chains produce selected frequency bin information produced by their respective FFT processors. The frequency samples selection per band processor accepts the frequency domain data produced by the FFT processor and selects only the frequency bins of interest in the received signal frequency spectrum. These selected frequency samples are provided to a normalized polarization vector computation per band block 714 that produces a value that corresponds to the location of the received signal's polarization on the Poincare' sphere. The normalized polarization vector computation per band block 714 produces values that correspond to the f1, f2, and f3 points on the Poincare sphere described above. These values are provided to a polarimetric trajectory mapping processor 716 that determines the trajectories, or displacements, between the transmitted and received polarizations at each transmitted frequency, i.e., those values that correspond to the diagonal values of the Polarization Trajectory State Space Matrix, "m" (i.e., f11, f22 and f33). The plarimetric trajectory mapping processor 716 also calculates the off-diagonal values of the Parization Trajectory State Space Matrix, "m" (i.e., f12, f23, f13, f31, f32, and f21).

The frequency domain received signal processing circuit 700 of the exemplary embodiment contains a vertical PN-sequence state generator 722 and a horizontal PN-sequence state generator 724. These PN state generators generate a PN sequence that matches the pseudo-noise sequence produced by the PN-sequence generator 608 of the frequency domain transmitted signal generation circuit 600. These PN-sequence state generators drive respective Pulse tables 718, 720, which define the amplitude and phase, and thus information sufficient to calculate the transmitted polarization profile, for each transmitted wavelength based upon the pseudorandom data produced by the vertical PN-sequence state generator 722 and the horizontal PN-sequence state generator 724. The outputs of these pulse tables 718, 720 are provided, along with the output of the polarimetric trajectory mapping processor 716, to a polarimetric trajectory correlation processor 726. The polarimetric trajectory correlation processor 726 corrects the output of the polarimetric trajectory correlation processor 726 for the transmitted polarization profile and correlates the observed polarization transformations with those stored in the polarization transformation to material mapping table 500 for the frequency set being transmitted. These correlations are provided to a material selection processor 728 that estimates the material from which the physical object is made. The material selection processor 728 of the exemplary embodiment determines this estimate based upon a best fit analysis of the polarization transformations for the transmitted frequency set.

Figure 8:
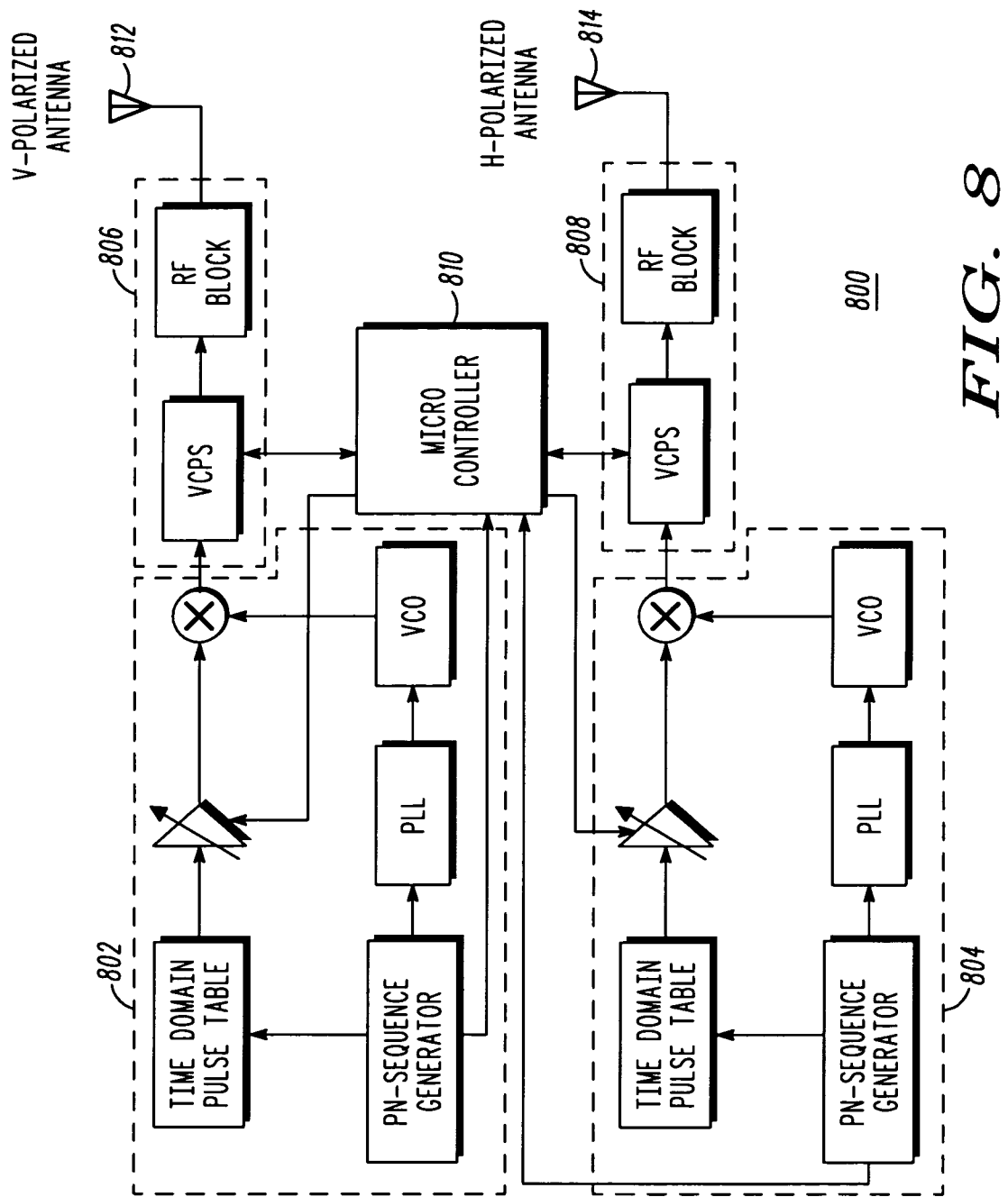
FIG. 8 illustrates a processing block diagram of a time domain transmitted signal generation circuit in accordance with a further embodiment of the present invention.

FIG. 8 illustrates a processing block diagram of a time domain transmitted signal generation circuit 800 in accordance with a further embodiment of the present invention. The time domain transmitted signal generation circuit 800 generates a transmitted electromagnetic signal 112 and allows specification of the time domain envelope and time varying frequency for that generated transmitted electromagnetic signal 112. The time domain transmitted signal generation circuit 600 includes a vertically polarized antenna 812 and a horizontally polarized antenna 814. The time domain transmitted signal generation circuit 800 independently generates two RF signals, one to be transmitted through the vertically polarized antenna 812 and another to be transmitted through the horizontally polarized antenna 814.

The time domain transmitted signal generation circuit 800 includes a vertical transmitted signal generator 802 and a horizontal transmitted signal generator 804. These transmitted signal generators includes a PN-sequence generator that is configured to generate two, independent PN-sequences to specify each of the amplitude and frequency of the generated transmitted signal. This allows the transmitted electromagnetic signal 112 to have a polarization profile that is based upon the PN-sequences generated by the PN-sequence generator. A local oscillator signal is generated within the transmitted signal generators by providing one PN-sequence to a Phase Locked Loop (PLL) oscillator that drives a Voltage Controlled Oscillator (VCO). The amplitude of the generated transmitted signal is determined by a separate PN-sequence provided to a time domain pulse table, whose output is based upon the input contained in its input PN-sequence. The time domain pulse table output is provided to a variable amplifier that controls the magnitude of that polarization as specified by controls received from microcontroller 810. The local oscillator is modulated with the amplitude information and provided to a respective RF strip 806, 808. A vertical RF strip 806 generated RF signals to transmit through the vertically polarized transmit antenna 812 and the horizontal RF strip 808 generates RF signals to transmit through the horizontally polarized transmit antenna. The RF strips 806, 808 include a Voltage Controlled Phase Shifter (VCPS) that shifts the RF phase according to control provided by microcontroller 810. The RF strips 806, 808 also each include an RF block to produce the high power RF signals for transmission. The PN sequence generated by the PN-sequence generators is also provided to the microprocessor in order to support amplitude and phase modulation of the transmitted waveform. The operation of the time domain transmitted signal generation circuit 800 allows different RF wavelengths to be transmitted during different time domain pulses, such as can be selected by various values contained in the PN-sequence.

Figure 9:
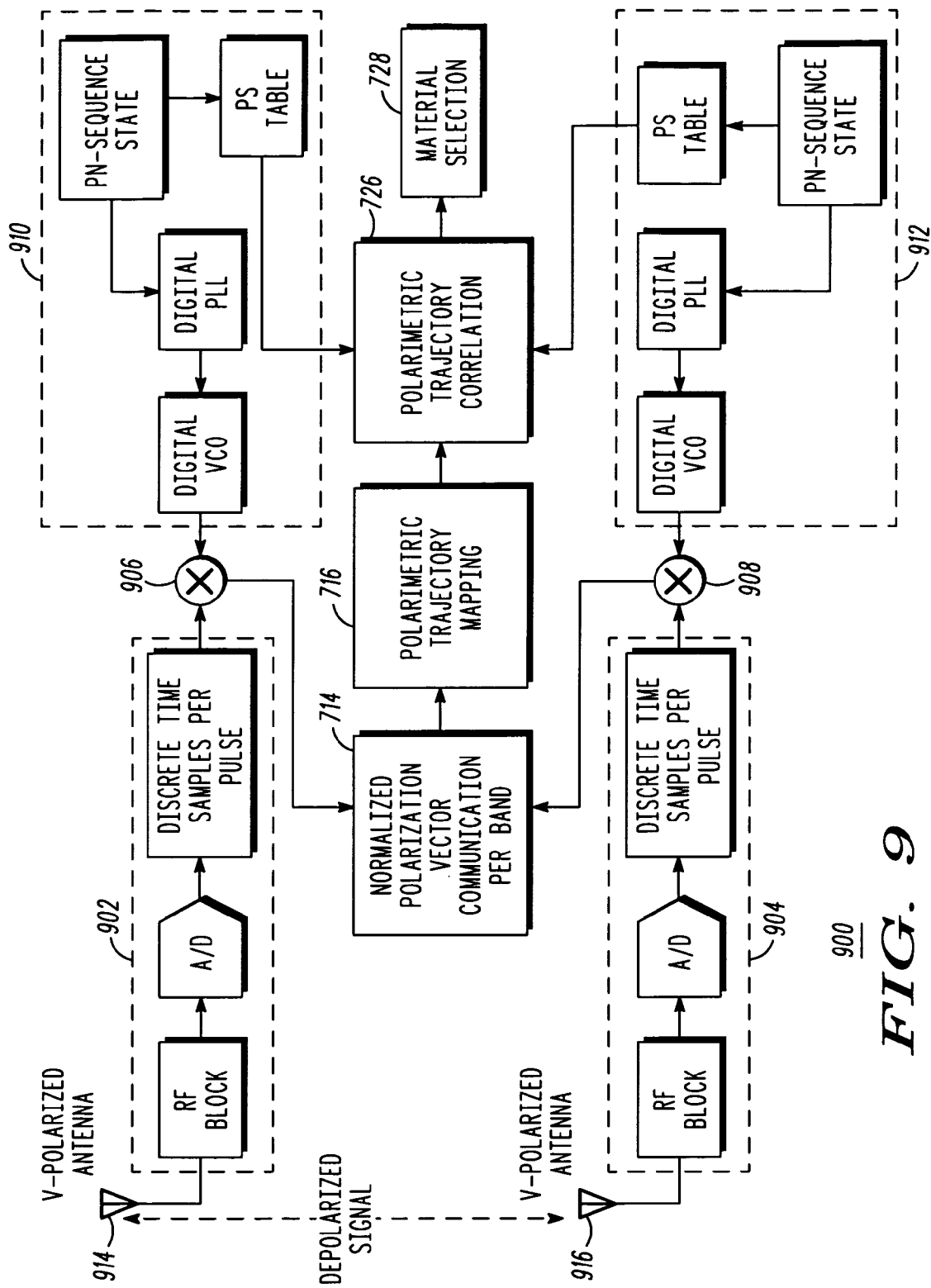
FIG. 9 illustrates a processing block diagram of a time domain received signal processing circuit in accordance with a further embodiment of the present invention.

FIG. 9 illustrates a processing block diagram of a time domain received signal processing circuit 900 in accordance with a further embodiment of the present invention. The time domain received signal processing circuit 900 receives signals that are reflected, refracted or diffracted by the physical object 102, depending upon the location of its receiving antennas. The time domain received signal processing circuit 900 includes receiving antennas that include a vertically polarized receiving antenna 914 and a horizontally polarized receiving antenna 916. The receiving antennas each drive a respective RF signal processing chain, a vertical RF processing chain 902 and a horizontal RF processing chain 904. Each RF processing chain includes an RF block, an Analog to Digital converter (A/D), and a discrete time samples per pulse processor. The RF processing chains produce discrete time samples per pulse that correspond with time samples of interest, such as intra-pulse time samples.

The time domain received signal processing circuit 900 also includes a transmitted signal synchronizer 910 that includes a PN-sequence state generator, Digital PLL, and a digital VCO to recreate the transmitted radio frequency profile of the transmitted electromagnetic signals 112 in the exemplary embodiment. The transmitted signal synchronizer 910 further includes a PS, or Polarization State, table that accepts the output of a PN-sequence state generator and defines the polarization state, or polarization profile, according to time and wavelength of the transmitted electromagnetic signals 112.

The recreated transmitted radio frequency profiles for the vertically polarized and horizontally polarized received signals are provided to respective downconverters 906, 908 to produce received baseband signals for the received vertical and horizontally polarized signals. These downconverted signals are provided to a normalized polarization vector computation per band block 714 that produces a value that corresponds to the location of the received signal's polarization on the Poincare' sphere, as is described above.

The outputs of the PS Tables of the transmitted signal synchronizer 910 are provided, along with the output of the polarimetric trajectory mapping processor 716, to a polarimetric trajectory correlation processor 726. The polarimetric trajectory correlation processor 726 determines the observed polarization transformations by comparing the respective received polarization for each transmitted wavelength to the predetermined transmitted polarization profile as is defined by the polarization states produced by the PS tables based upon its synchronized PN-sequence input. The polarimetric trajectory correlation processor 726 correlates the observed polarization transformations with those stored in the polarization transformation to material mapping table 500 for the frequency set being transmitted. These correlations are provided to a material selection processor 728 that estimates the material from which the physical object is made. The material selection processor 728 of the exemplary embodiment determines this estimate based upon a best fit analysis of the polarization transformations for the transmitted frequency set.

Figure 10:
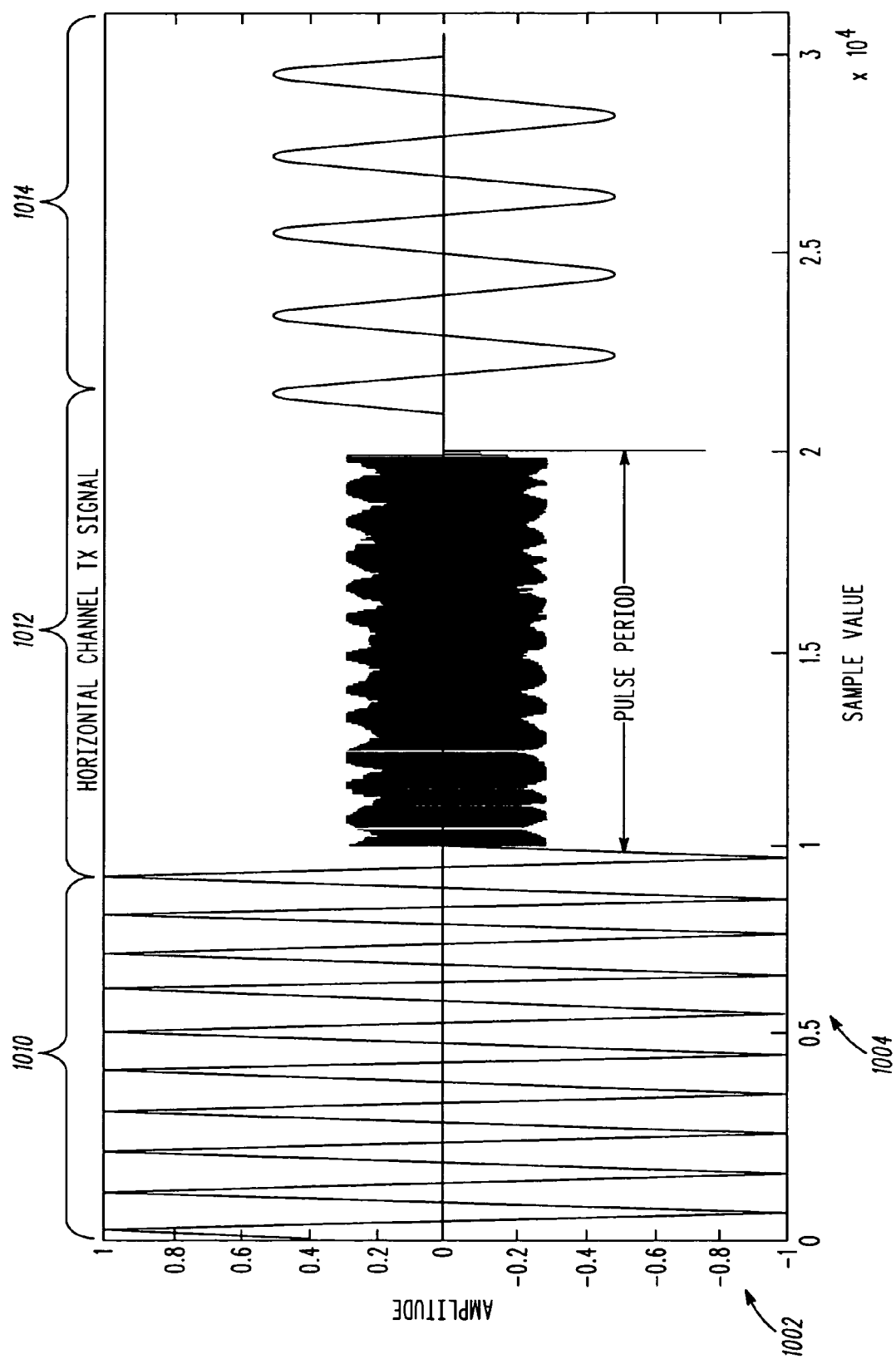
FIG. 10 illustrates a time domain representation of a horizontally polarized component of a transmitted signal generated by the circuits of FIGS. 6 and 8 in accordance with exemplary embodiments of the present invention.

FIG. 10 illustrates a time domain representation of a horizontally polarized component 1000 of a transmitted signal generated by the circuits of FIGS. 6 and 8 in accordance with exemplary embodiments of the present invention. The horizontally polarized component 1000 is illustrated in the context of an amplitude axis 1002 and a "sample value" axis 1004 that corresponds to time. The horizontally polarized component 1000 of this example consists of three time periods during each of which a different wavelength is transmitted. A first time period 1010 shows that an intermediate radio frequency, or wavelength, is transmitted with relatively large amplitude. A second time period 1012 shows that a high frequency is transmitted with a lower amplitude. A third time period 1014 shows that a low frequency is transmitted with an intermediate amplitude. This waveform is an example of a transmitted electromagnetic signal that includes the three wavelengths described in the example above.

Figure 11:
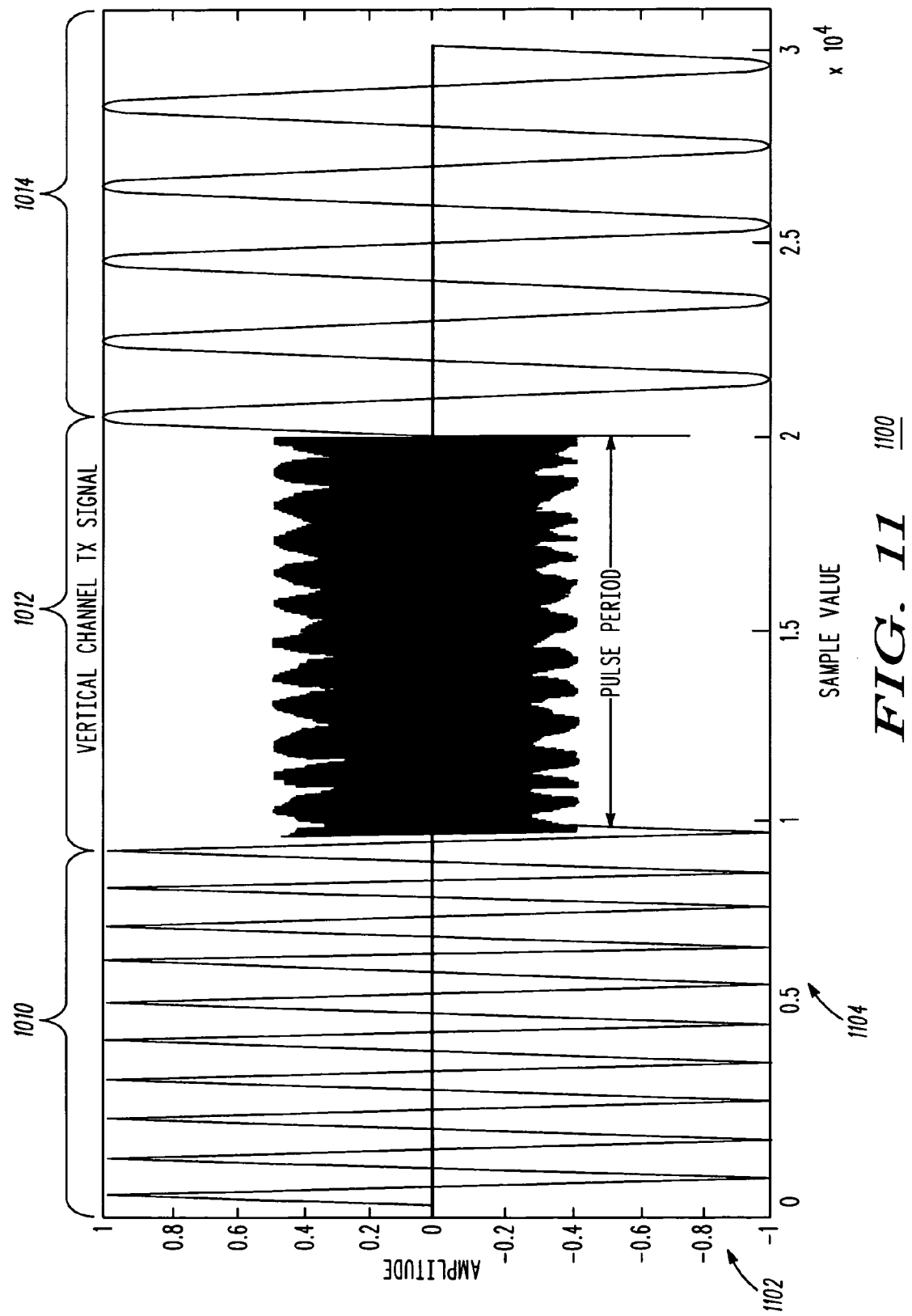
FIG. 11 illustrates a time domain representation of a vertically polarized component of a transmitted signal generated by the circuits of FIGS. 6 and 8 in accordance with exemplary embodiments of the present invention.

FIG. 11 illustrates a time domain representation of a vertically polarized component 1100 of a transmitted signal generated by the circuits of FIGS. 6 and 8 in accordance with exemplary embodiments of the present invention. The vertically polarized component 1100 is transmitted in time synchronization with the horizontally polarized component 1000. The amplitude and phase differences between the horizontally polarized component 1000 and the vertically polarized component 1100 produce pre-determined polarization profile for the transmitted electromagnetic signals 112.

Figure 12:
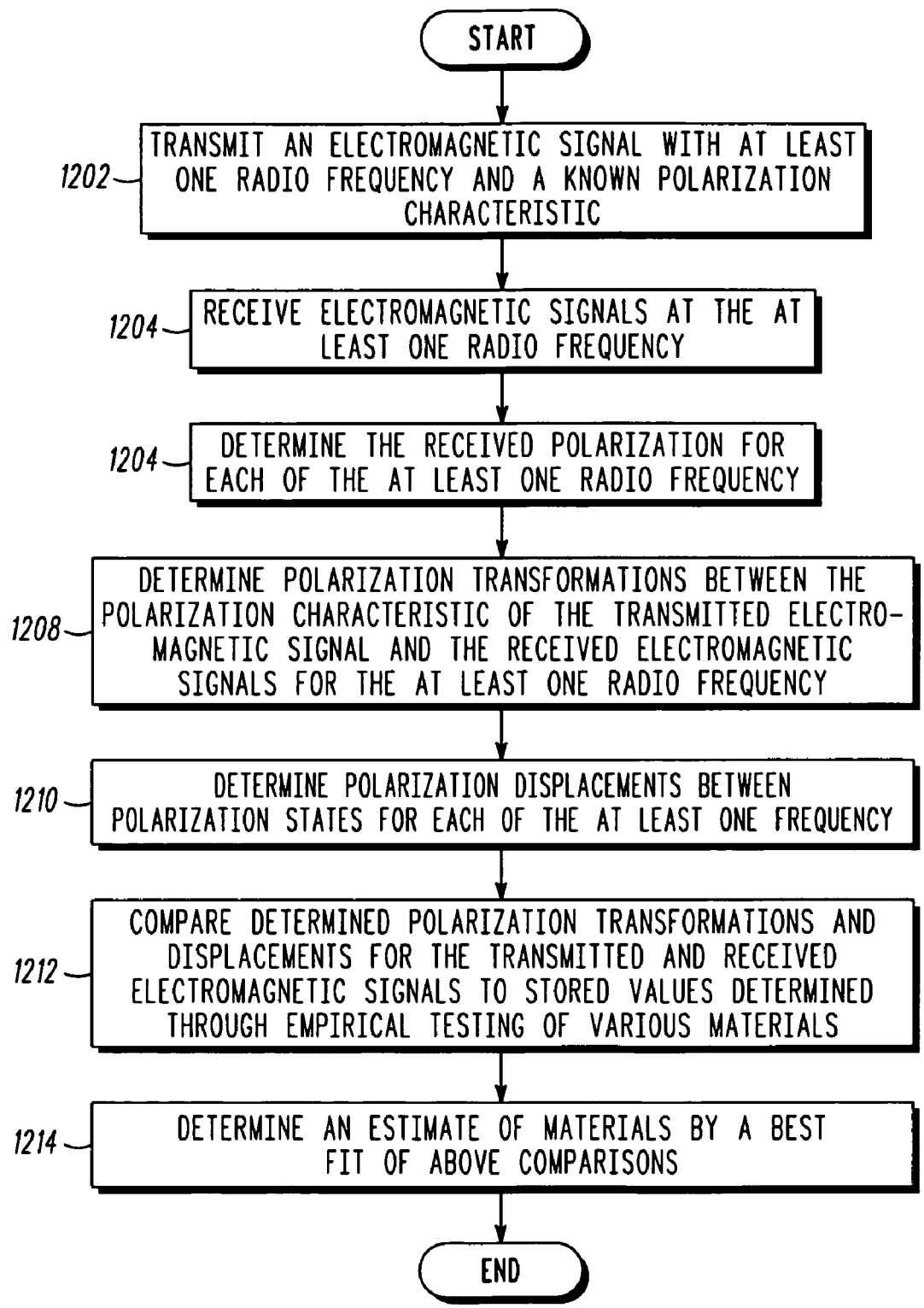
FIG. 12 illustrates a material estimation processing flow diagram 1200 in accordance with an exemplary embodiment of the present invention.

FIG. 12 illustrates a material estimation processing flow diagram 1200 in accordance with an exemplary embodiment of the present invention. The material estimation processing flow 1200 begins by transmitting, at step 1202, an electromagnetic signal with at least one wavelength and a known polarization characteristic. The processing then receives, at step 1204, electromagnetic signals with the same at least one wavelength. These signals are reflected, refracted, or diffracted by a physical object whose composition material is to be estimated. The processing next determines, at step 1206, the received polarization for each of the at least one wavelengths. The processing next determines, at step 1208, the polarization transformations, for each of the at least one transmitted wavelengths, between the polarization characteristic of the transmitted electromagnetic signal and the received electromagnetic signals. The processing further determines, at step 1210, the polarization displacements between polarization states for each of the at least one transmitted wavelength. The processing continues by comparing, at step 1212, the polarization transformations and displacements that were determined between the transmitted and received electromagnetic signals, as well as the displacements between received polarizations of the different frequencies within the at least one frequency, to stored values. These stored values in the exemplary embodiment were determined through empirical means for a variety of materials. The processing then determines, at step 1214, an estimate of the material composition by calculating a best fit estimate between the determined and stored values. The processing then terminates.

Figure 13:
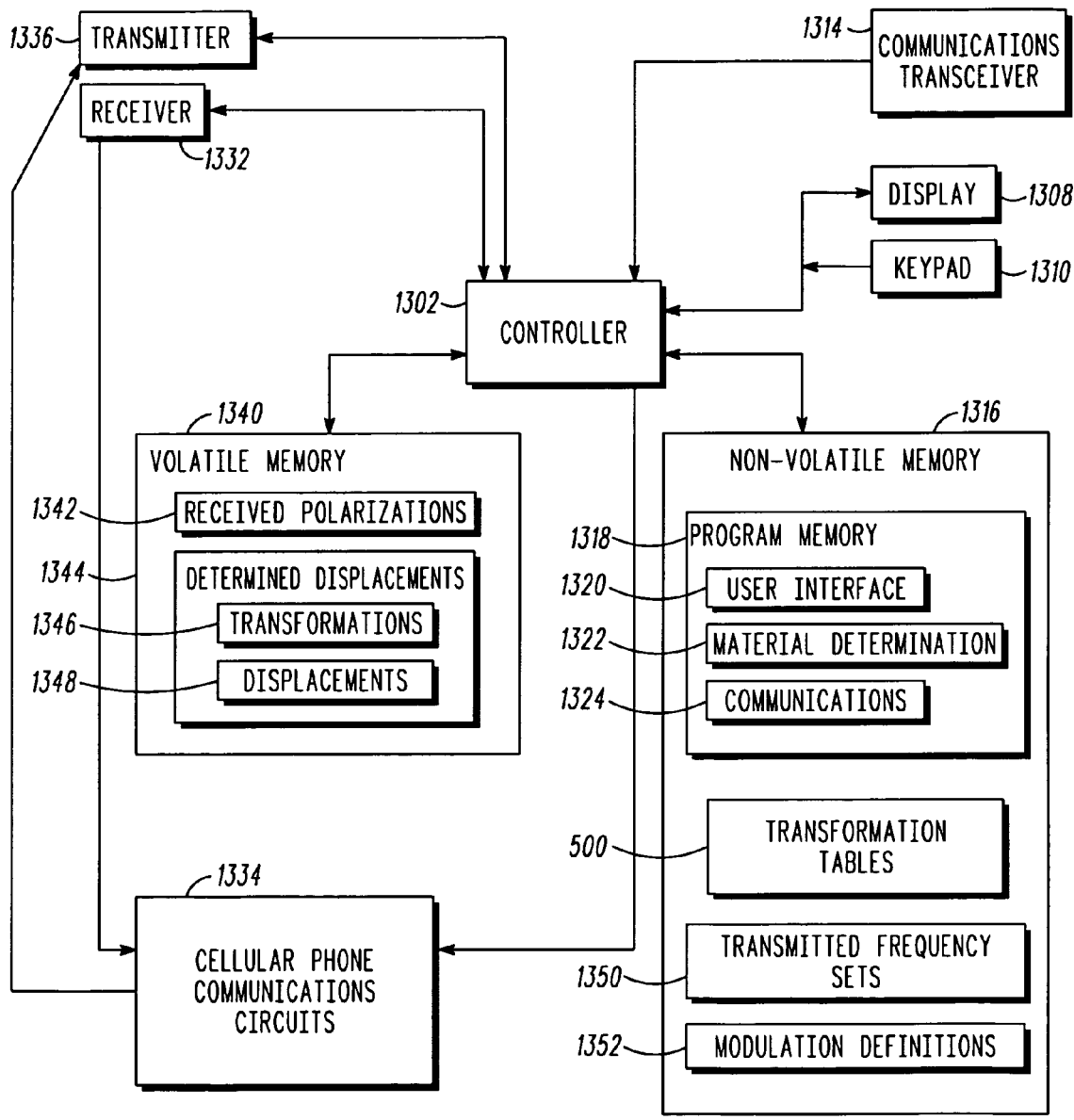
FIG. 13 illustrates a processing circuit block diagram for a material detection system 1300, in accordance with one embodiment of the present invention.

FIG. 13 illustrates a processing circuit block diagram for a material detection system 1300, in accordance with one embodiment of the present invention. The material detection system includes a transmitter 1336, such as the frequency domain transmitted signal generation circuit 600 or the time domain transmitted signal generation circuit 800, described above. The material detection system includes a receiver 1312, such as the frequency domain received signal processing circuit 700 or the time domain received signal processing circuit 900, described above. The material detection system 1300 further includes a communications transceiver 1314 to support either voice or data communications. The communications transceiver is used to support communications between, for example, a signal transceiver 104 and one or more remote receivers 110. The communications transceiver is also able to communicate estimated material content to a central server, such as to support automatic alarm generation.

A programmable controller 1302 provides the central control for the material detection system and includes a programmable microprocessor and is able to also contain other programmable and optionally fixed logic control circuits as are required for proper operation of the material detection system. Controller 1302 performs, for example, the processing associated with the material detection methods described above.

The material detection system 1300 further has a user interface that includes a display 1308 and keypad 1310. The keypad 1310 is used to accept inputs to control the operation of the material detection system 1300 from the user. Display 1310 provides alpha-numeric output to the user, such as a description of the detected material.

The controller 1302 of the exemplary embodiment stores and retrieves data from volatile memory 1340 and non-volatile memory 1316. The non-volatile memory 1316 of the exemplary embodiment retains its data when the remote controller is powered off. The non-volatile memory 1316 is normally used to store information that is to be retained for long time periods, but the non-volatile memory 1316 is also able to be reprogrammed by controller 1302 or by external equipment. Data stored in volatile memory 1340 is normally used for a short period of time while the remote controller is operating. Embodiments of the present invention are able to store data in any of volatile and non-volatile memory according to their design and the storage of data described below is not a limiting example of these options.

The volatile memory 1340 of the exemplary embodiment is used to store determined received polarizations data 1342 and determined displacements data 1344. The determined received polarization data 1342 contains the received polarizations for each of the transmitted frequencies as determined by the processing of receiver 1312. The determined displacement data 1344 contains the polarization displacements between the received polarizations for each received frequency, as is described above. The determined displacements data 1344 of this exemplary embodiment includes transformations 1346 and displacements 1348. The transformations 1346 include the polarization transformations observed between the transmitted electromagnetic signal 112 and the received electromagnetic signals, such as the reflected electromagnetic signal 116 and the refracted/diffracted electromagnetic signal 118. Data stored in the displacement data 1348 describes the polarization displacement vectors between the polarizations of the different received frequencies.

The non-volatile memory includes a program memory 1318 that stores the operational computer program executed by the controller 1302. Included in the program memory 1318 of the exemplary embodiment is a user interface program 320 that controls the user interface elements of the remote controller.

The program memory further includes a communications program 1324 that is used to implement communications through the communications transceiver 1314 of the exemplary embodiment, such as for communicating data between the signal transceiver 104 and remote receivers 110. The program memory also includes the material determination processing program 1322 that performs the material determination processing described above.

The non-volatile memory 1316 includes transformation tables 500, similar to the transformation tables 500 described above. In the exemplary embodiment, transformation data for several hundreds, thousands or more types of materials are stored in the transformation tables 500 to support identification of a multitude of different materials. The non-volatile memory of the exemplary embodiment further includes transmitted frequency sets 1350 and modulation definitions 1352. The transmitted frequency sets 1350 and modulation definitions 1352 define the transmitted frequencies and modulation formats used to determine material types.

The material detection system 1300 of the exemplary embodiment is contained within a cellular telephone. The material detection system 1300 includes cellular telephone circuits 1334 that perform processing required to communicate over a cellular telephone network. The cellular telephone circuits 1334 of the exemplary embodiment are able to use the transmitter 1336 and receiver 1332 to perform radio frequency transmission and reception, respectively, as required for cellular telephone communications. The design of the exemplary embodiments of the present invention advantageously allow incorporate of the material detection system 1300 into a housing similar to that used for conventional cellular telephones. Further, material detection systems 1300 of the exemplary embodiments of the present invention are able to communicate data over the cellular telephone circuits 1334 so as to allow one material detection system 1300 to function as a signal transceiver 104 while other nearby material detection systems 1300 are able to function as remote receivers 110 and communicate their polarization measurements back to the signal transceiver 104 to support material estimation processing.

Some embodiments of the present invention limit the received electromagnetic signal data that is processed by performing time gating of received signals that are processed. The received signals that are processed are also limited in some embodiments by limiting the angle of arrival of received signals that are processed. These two limitations reduce signal "clutter" that may invalidate measurements made by the receiving system. For example, time gating allows rejection of received signals that were reflected by an object that is outside the area of interest containing objects to be identified. Limiting the processing of received signals to only those signals received within a narrow angle of arrival is able to reduce processing of signals that are reflected by multiple surfaces, such as walls in the area of the object being processed. Time gating is implemented in some embodiments by only accepting received signals into at least one component of the processing chain during a pre-determined time. Angle of arrival limiting is performed in some embodiments, for example, by using a directional antenna.

The operation of the exemplary embodiment is further able to be used with multiple receivers. These multiple receivers are able to each provide a polarization transformation for the received signal relative to the transmitted signal, and provide their respective material composition estimation. The polarization transformation and/or the material composition estimations determined by each of these multiple receivers are able to be assembled into a central processor and compared or otherwise statistically processed to determine a most likely estimate of material composition based upon the multiple observations, some of which may be inconsistent with other observations. The material estimation process is also able to be assisted in some embodiments of the present invention by limiting the number of candidate materials for the object 102.

The terms program, software application, and the like as used herein, are defined as a sequence of instructions designed for execution on a computer system. A program, computer program, or software application may include a subroutine, a function, a procedure, an object method, an object implementation, an executable application, an applet, a servlet, a source code, an object code, a shared library/dynamic load library and/or other sequence of instructions designed for execution on a computer system.

Reference throughout the specification to "one embodiment" means that a particular feature, structure, or characteristic described in connection with the embodiment is included in at least one embodiment of the present invention. Thus, the appearances of the phrases "in one embodiment" in various places throughout the specification are not necessarily all referring to the same embodiment. Furthermore, the particular features, structures, or characteristics may be combined in any suitable manner in one or more embodiments. Moreover these embodiments are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in the plural and visa versa with no loss of generality.

While the various embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims.

What is claimed is:

1. A method for determining a most likely material composition of an object, the method comprising:
   storing, for at least one material composition, at least one respective stored radiation polarization transformation at a plurality of wavelengths for each of the material compositions within the at least one material composition;
   receiving a received signal, the received signal corresponding to a transmitted electromagnetic signal that was transmitted by a transmitter towards an object, the transmitted electromagnetic signal having a known transmitted polarization profile;
   determining a respective received polarization for each of at least one wavelength of the received signal that has encountered the object, the received signal comprising a portion of the transmitted electromagnetic signal that has encountered the object;
   determining, for each of the at least one wavelength, at least one calculated polarization transformation based upon at least one polarization trajectory between the transmitted polarization profile and the respective received polarization for at least one of the at least one wavelength of the received signal;
   comparing, for each of the at least one wavelength, the respective calculated polarization transformations to the at least one respective stored radiation polarization transformations for at least one of the plurality of material compositions;
   estimating, based on the comparing, a most likely material composition for the object; and
   outputting an indication of the most likely material composition.

2. The method according to claim 1,
   wherein each of the at least one stored radiation polarization transformations and each of the calculated polarization transformations is represented as Stoke's parameters, and
   wherein the comparing comprises comparing the Stoke's parameters of the stored radiation polarization transformations to the Stoke's parameters of the calculated polarization transformations.

3. The method according to claim 1, further comprising:
   storing polarization displacement data for at least two of the plurality of wavelengths, the polarization displacement data describing differences between at least two of the calculated polarization transformations between at least two respective wavelengths within the plurality of wavelengths for at least one of the plurality of material compositions;
   determining at least one determined polarization displacement, the determined polarization displacement representing a polarization displacement between a first received signal component within the received signal at the first wavelength and a second received signal component within the received signal at the second wavelength; and
   comparing, for at least two of the plurality of wavelengths, the respective at least one determined polarization displacement to the respective stored polarization displacement data, and
   wherein the estimating is further based upon the comparing the respective at least one determined polarization displacement to the respective stored polarization displacement.

4. The method according to claim 1, wherein at least two wavelengths of the plurality of wavelengths are selected based upon an amount of polarization transformation for at least one of the at least one material composition for each of the two wavelengths.

5. The method according to claim 1, wherein the transmitted electromagnetic signal comprises a plurality of discrete RF carriers.

6. The method according to claim 1, wherein the transmitted electromagnetic signal comprises at least two wavelengths transmitted with substantially equal polarization.

7. The method according to claim 1, wherein the transmitted polarization profile varies over time based upon a pseudorandom data sequence.

8. The method according to claim 1, wherein the transmitted electromagnetic signal comprises a sequence of pulse transmissions.

9. The method according to claim 1, wherein the transmitted electromagnetic signal comprises a sequence of pulsed radio frequency transmissions with at least one of pulse duration, wavelength, and pulse period varying based upon a pseudorandom data sequence.

10. The method according to claim 1, further comprising transmittin the transmitted electromagnetic signal, wherein the transmitting is performed through at least one antenna, and wherein the object is within a near field of at least one of the at least one antenna.

11. The method according to claim 1, further comprising:
    transmitting the transmitted electromagnetic signal with at least one transmitting antenna, each of the at least one transmitting antenna located at a respective transmitting location,
    receiving the received signal with at least one receiving antenna, each of the at least one receiving antenna being located at a respective receiving location, and
    wherein at least one of the respective receiving locations is removed from the respective transmitting locations.

12. The method according to claim 11, wherein the receiving is performed at a plurality of locations to produce a plurality of received signals,
    wherein the comparing is performed for each received signal within the plurality of received signals, and
    wherein the estimating comprises statistically processing results of the comparing to determine a most likely material composition.

13. The method according to claim 1, wherein the transmitted electromagnetic signal is modulated by a pre-determined waveform and wherein the stored at least one respective stored radiation polarization transformation comprises at least one radiation polarization transformation that corresponds to an electromagnetic signal at one of the at least one wavelengths that is modulated by the pre-determined waveform.

14. The method according to claim 13, wherein the pre-determined waveform is based upon a pseudo-noise data sequence and modulates the transmitted polarization profile.

15. A material determination system used to determine a most likely material composition of an object, the material determination system comprising:
- a stored transformation database that stores, for at least one material composition, at least one respective stored radiation polarization transformation at a plurality of wavelengths for each of the material compositions within the at least one material composition;
- a receiver that receives a received signal, the received signal corresponding to a transmitted electromagnetic signal that was transmitted by a transmitter towards an object, the transmitted electromagnetic signal having a known transmitted polarization profile; and
- a material composition estimator that:
- determines a respective received polarization for each of the at least one wavelength of the received signal that has encountered the object, the received signal comprising a portion of the transmitted electromagnetic signal that has encountered the object;
- determines, for each of the at least one wavelength, a respective calculated polarization transformation based upon at least one polarization trajectory between the transmitted polarization profile and the respective received polarization for at least one of the at least one wavelength of the received signal;
- compares, for each of the at least one wavelength, the respective calculated polarization transformations to the at least one respective stored radiation polarization transformations for at least one of the plurality of material compositions;
- estimates, based on the comparing, a most likely material composition for the object; and
- an estimate output adapted to outputting an indication of the most likely material composition.

16. The material determination system according to claim 15, wherein the receiver is located remotely from the transmitter.

17. The material determination system according to claim 15, wherein the material composition estimator comprises a radio receiver adapted to receive the received signal, the material determination system further comprising a cellular telephone enclosure, the cellular telephone enclosure containing:
- the transmitter;
- the receiver; and
- a cellular telephone communications circuits to support at least one of data communications and voice communications in conjunction with the transmitter and the receiver.

18. A computer program product comprising machine readable instructions for determining a most likely material composition of an object, the machine readable instructions comprising instructions for:
- storing, for at least one material composition, at least one respective stored radiation polarization transformation at a plurality of wavelengths for each of the material compositions within the at least one material composition;
- receiving a received signal, the received signal corresponding to a transmitted electromagnetic signal that was transmitted by a transmitter towards an object, the transmitted electromagnetic signal having a known transmitted polarization profile;
- determining a respective received polarization for each of at least one wavelength of a received signal that has encountered the object, the received signal comprising a portion of the transmitted electromagnetic signal that has encountered the object;
- determining, for each of the at least one wavelength, at least one calculated polarization transformation based upon at least one polarization trajectory between the transmitted polarization profile and the respective received polarization for at least one of the at least one wavelength of the received signal;
- comparing, for each of the at least one wavelength, the respective calculated polarization transformations to the at least one respective stored radiation polarization transformations for at least one of the plurality of material compositions; and
- estimating, based on the comparing, a most likely material composition for the object; and
- outputting an indication of the most likely material composition.

19. The method according to claim 1, further comprising transmitting the transmitted electromagnetic signal.

20. The material determination system according to claim 15, further comprising the transmitter adapted to transmit the transmitted electromagnetic signal.

* * * * *